(12) United States Patent
Lintereur et al.

(10) Patent No.: US 11,660,394 B2
(45) Date of Patent: May 30, 2023

(54) FLUID INFUSION SYSTEM THAT AUTOMATICALLY DETERMINES AND DELIVERS A CORRECTION BOLUS

(71) Applicant: Medtronic MiniMed, Inc., Northridge, CA (US)

(72) Inventors: Louis J. Lintereur, Boise, ID (US); Anirban Roy, Agoura Hills, CA (US); Benyamin Grosman, Winnetka, CA (US); Patrick E. Weydt, Moorpark, CA (US); Neha J. Parikh, West Hills, CA (US); Di Wu, Glendale, CA (US); Ali Dianaty, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 345 days.

(21) Appl. No.: 17/122,445

(22) Filed: Dec. 15, 2020

(65) Prior Publication Data

US 2021/0093783 A1 Apr. 1, 2021

Related U.S. Application Data

(63) Continuation of application No. 16/275,290, filed on Feb. 13, 2019, now Pat. No. 10,894,126.
(Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC . A61B 5/14532; A61B 5/4848; A61B 5/4866; A61M 2005/14208;
(Continued)

(56) References Cited

U.S. PATENT DOCUMENTS 4,562,751 A 7/1986 Nason et al.
4,685,903 A 11/1987 Cable et al.
(Continued)

OTHER PUBLICATIONS

International Preliminary Report on Patentability from International Application No. PCT/US2019/035628, dated Apr. 8, 2021, 9 pp.
(Continued)

*Primary Examiner* — Deanna K Hall
(74) *Attorney, Agent, or Firm* — Shumaker & Sieffert, P.A.

(57) ABSTRACT

A method of controlling an insulin infusion device involves controlling the device to operate in an automatic basal insulin delivery mode, obtaining a blood glucose measurement for the user, and initiating a correction bolus procedure when: the measurement exceeds a correction bolus threshold value; and a maximum basal insulin infusion rate is reached during the automatic basal insulin delivery mode. The correction bolus procedure calculates an initial correction bolus amount, and scales the initial amount to obtain a final correction bolus amount, such that a predicted future blood glucose level resulting from simulated delivery of the final correction bolus amount exceeds a low blood glucose threshold level. The final amount is delivered to the user during operation in the automatic basal insulin delivery mode.

20 Claims, 11 Drawing Sheets

Related U.S. Application Data

(60) Provisional application No. 62/739,009, filed on Sep. 28, 2018.

(51) Int. Cl.
*A61B 5/00* (2006.01)
*G16H 20/17* (2018.01)

(52) U.S. Cl.
CPC .......... *A61B 5/4866* (2013.01); *A61B 5/7275* (2013.01); *G16H 20/17* (2018.01); *A61M 2205/3303* (2013.01); *A61M 2205/52* (2013.01); *A61M 2230/201* (2013.01)

(58) Field of Classification Search
CPC ...... A61M 2205/3303; A61M 2205/50; A61M 2205/52; A61M 2230/201; A61M 5/14244; A61M 5/1723
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,522,803 A | 6/1996 | Teissen-Simony |
| 5,505,709 A | 9/1996 | Funderburk et al. |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,641,533 B2 | 4/2003 | Causey, III et al. |
| 6,558,320 B1 | 6/2003 | Causey, III et al. |
| 6,558,351 B1 | 6/2003 | Steil et al. |
| 6,589,229 B1 | 7/2003 | Connelly et al. |
| 6,591,876 B2 | 7/2003 | Safabash |
| 6,659,980 B2 | 9/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 2007/0123819 A1 | 5/2007 | Mernoe et al. |
| 2010/0160861 A1 | 6/2010 | Causey, III et al. |
| 2014/0066886 A1 | 3/2014 | Roy et al. |
| 2014/0066888 A1 | 3/2014 | Parikh et al. |
| 2014/0066889 A1 | 3/2014 | Grosman et al. |
| 2018/0200438 A1 | 7/2018 | Mazlish et al. |
| 2020/0101222 A1 | 4/2020 | Lintereur et al. |

OTHER PUBLICATIONS

Prosecution History from U.S. Appl. No. 16/275,290, dated Sep. 15, 2020 through Sep. 23, 2020, 10 pp.
International Search Report and Written Opinion of International Application No. PCT/US2019/035628, dated Sep. 23, 2019, 11 pp.

FLUID INFUSION SYSTEM THAT AUTOMATICALLY DETERMINES AND DELIVERS A CORRECTION BOLUS

CROSS-REFERENCE TO RELATED APPLICATION

This application is a continuation of U.S. application Ser. No. 16/275,290, which was filed on Feb. 13, 2019 and claims the benefit of U.S. provisional patent application Ser. No. 62/739,009, filed Sep. 28, 2018, the entire content of each of which is incorporated herein by reference.

TECHNICAL FIELD

Embodiments of the subject matter described herein relate generally to drug delivery systems and, more specifically, to systems for controlling the operation of an insulin infusion device that delivers insulin to the body of a patient.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a fluid reservoir that delivers medication from the reservoir to the body of a patient via a fluid path created between the reservoir and the body of a patient. Use of infusion pump therapy has been increasing, especially for delivering insulin for diabetics.

Control schemes have been developed to allow insulin infusion pumps to monitor and regulate a patient's blood glucose level in a substantially continuous and autonomous manner. Managing a diabetic's blood glucose level is complicated by variations in a patient's daily activities (e.g., exercise, carbohydrate consumption, and the like) in addition to variations in the patient's individual insulin response and potentially other factors. Some control schemes may attempt to proactively account for daily activities to minimize glucose excursions. At the same time, patients may manually initiate delivery of insulin prior to or contemporaneously with consuming a meal (e.g., a meal bolus or correction bolus) to prevent spikes or swings in the patient's blood glucose level that could otherwise result from the impending consumption of carbohydrates and the response time of the control scheme. That said, a manually-initiated bolus could introduce a risk of a postprandial glucose excursion if preceding insulin deliveries are not accounted for.

An insulin infusion pump can be operated in an automatic mode wherein basal insulin is delivered at a rate that is automatically adjusted for the user. While controlling the delivery of basal insulin in this manner, the pump can also control the delivery of correction boluses to account for rising glucose trends, a sudden spike in detected blood glucose, etc. Ideally, the amount of a correction bolus should be accurately calculated and administered to maintain the user's blood glucose within the desired range. In particular, an automatically generated and delivered correction bolus should safely manage the user's blood glucose level and keep it above a defined threshold level. Accordingly, there is a need to improve the handling of correction boluses that are delivered during an automatic mode of an insulin infusion pump.

BRIEF SUMMARY

A method of controlling operation of an insulin infusion device is disclosed here. The insulin infusion device includes a fluid reservoir for insulin to be delivered from the insulin infusion device to a body of a user, and has at least one processor device to perform the method. The method involves the steps of: controlling the insulin infusion device to operate in an automatic basal insulin delivery mode; obtaining a blood glucose measurement that indicates a current blood glucose level of the user; and initiating a correction bolus procedure when: (1) the blood glucose measurement exceeds a correction bolus threshold value; and (2) a maximum allowable basal insulin infusion rate (Umax) has been reached during operation in the automatic basal insulin delivery mode. The correction bolus procedure involves the steps of: calculating an initial correction bolus amount for the user; scaling the initial correction bolus amount to obtain a final correction bolus amount for the user, such that a predicted future blood glucose level of the user resulting from simulated delivery of the final correction bolus amount exceeds a low blood glucose threshold level; and delivering the final correction bolus amount to the body of the user during operation in the automatic basal insulin delivery mode.

An insulin infusion device is also disclosed here. The insulin infusion device includes: a fluid reservoir for insulin to be delivered from the insulin infusion device to a user; at least one processor device; and at least one memory element associated with the at least one processor device. The at least one memory element stores processor-executable instructions configurable to be executed by the at least one processor device to perform the method summarized in the preceding paragraph.

Also disclosed here is a tangible and non-transitory electronic storage medium having processor-executable instructions configurable to be executed by at least one processor device to perform the method summarized above.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
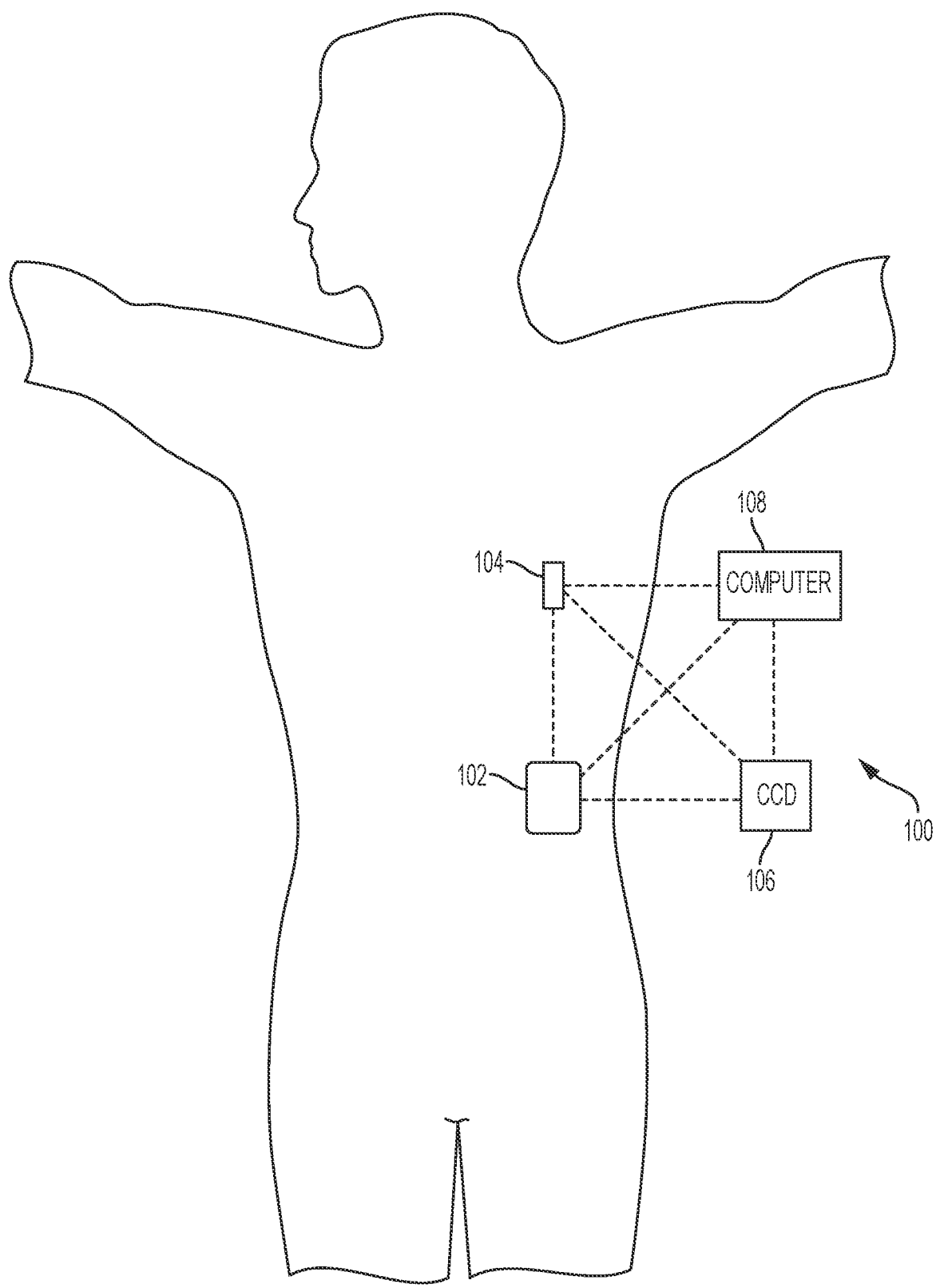
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter may be implemented in an equivalent manner in the context of other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication.

Generally, a fluid infusion device includes a motor or other actuation arrangement that is operable to linearly displace a plunger (or stopper) of a fluid reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop or automatic operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments of the subject matter described herein generally relate to proactively adjusting correction bolus amounts that are administered during automated operation of an insulin infusion device. As described in greater detail below, in exemplary embodiments, one or more mathematical models for the patient's physiological response are utilized to predict or forecast future glucose levels for a patient based on the patient's current and/or recent glucose measurements, preceding insulin deliveries, manually-input carbohydrate amounts, meal boluses, and a calculated correction bolus amount. When the patient's predicted future glucose level using the initial correction bolus amount is below a threshold value within a specified time window, the initial correction bolus amount is reduced to an amount that results in the patient's predicted future glucose level being maintained above that threshold value. In exemplary embodiments, the initial correction bolus value is progressively or iteratively scaled down to reduce the bolus amount as needed. In certain exemplary embodiments, the scaling methodology attempts to maximize the correction bolus dosage within the search space defined by the initial correction bolus amount while maintaining a predicted future glucose level for the patient that satisfies the designated hypoglycemic threshold during the time period of interest.

By virtue of the physiological model for the patient's predicted future glucose level accounting for the preceding automated or autonomous insulin deliveries along with the patient's current glucose level and the current trend in the patient's glucose level, the adjusted correction bolus amount reduces the risk of a post-bolus hypoglycemic event. For example, in some embodiments, closed-loop control information may be automatically adjusted in advance of an anticipated event likely to influence the patient's glucose levels or insulin response. In this regard, prospective closed-loop control adjustments account for the relatively slow action of long-acting subcutaneously administered insulin by adjusting insulin delivery in advance of an event to increase or decrease the amount of yet to be metabolized insulin on board prior to start of the event. Thus, the adjusted bolus amount accounts for prospective closed-loop insulin deliveries in a manner that reduces the risk of a post-bolus glucose excursion.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
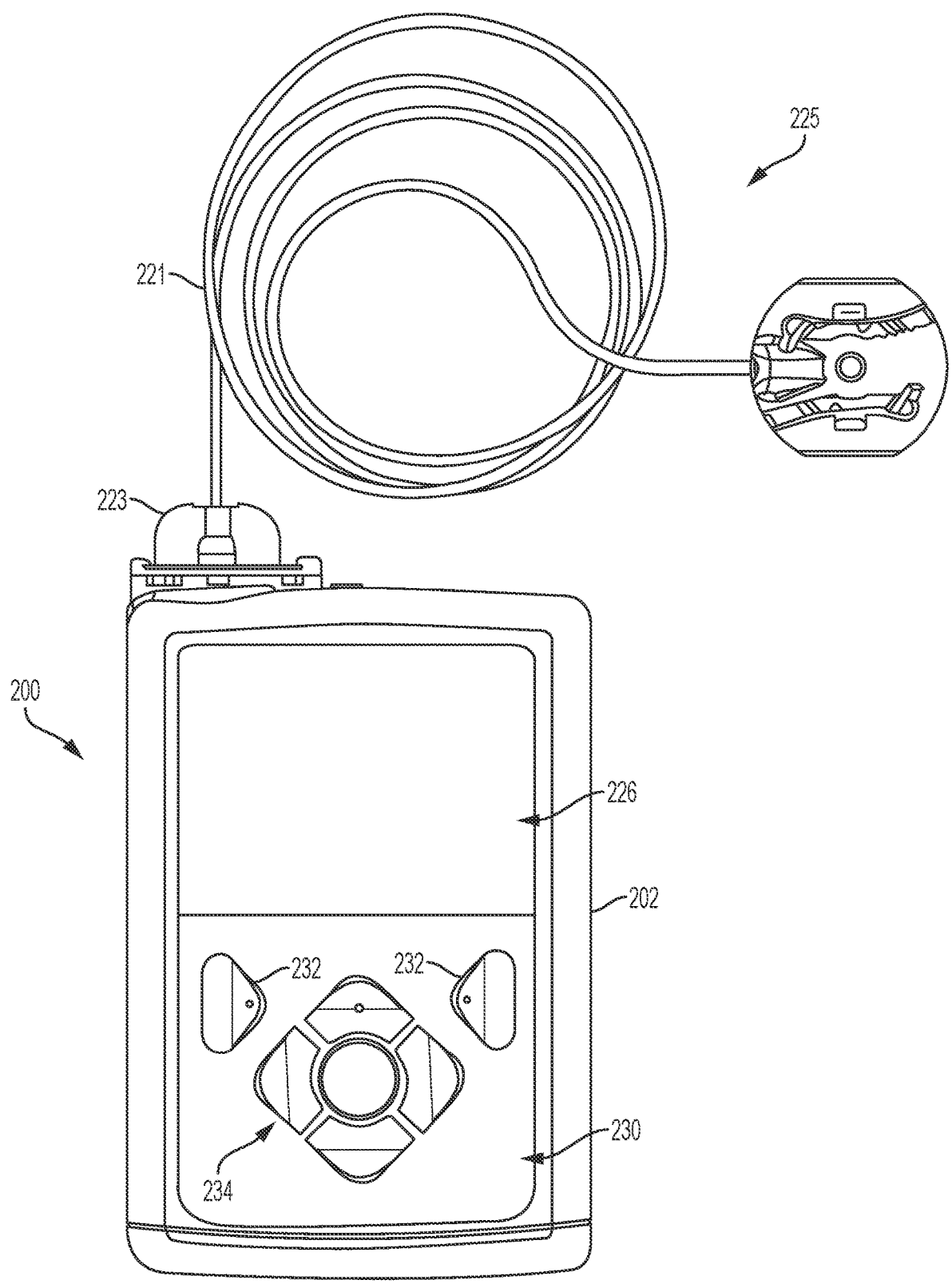
FIG. 2 depicts a plan view of an exemplary embodiment of a fluid infusion device suitable for use in the infusion system of FIG. 1.
Figure 3:
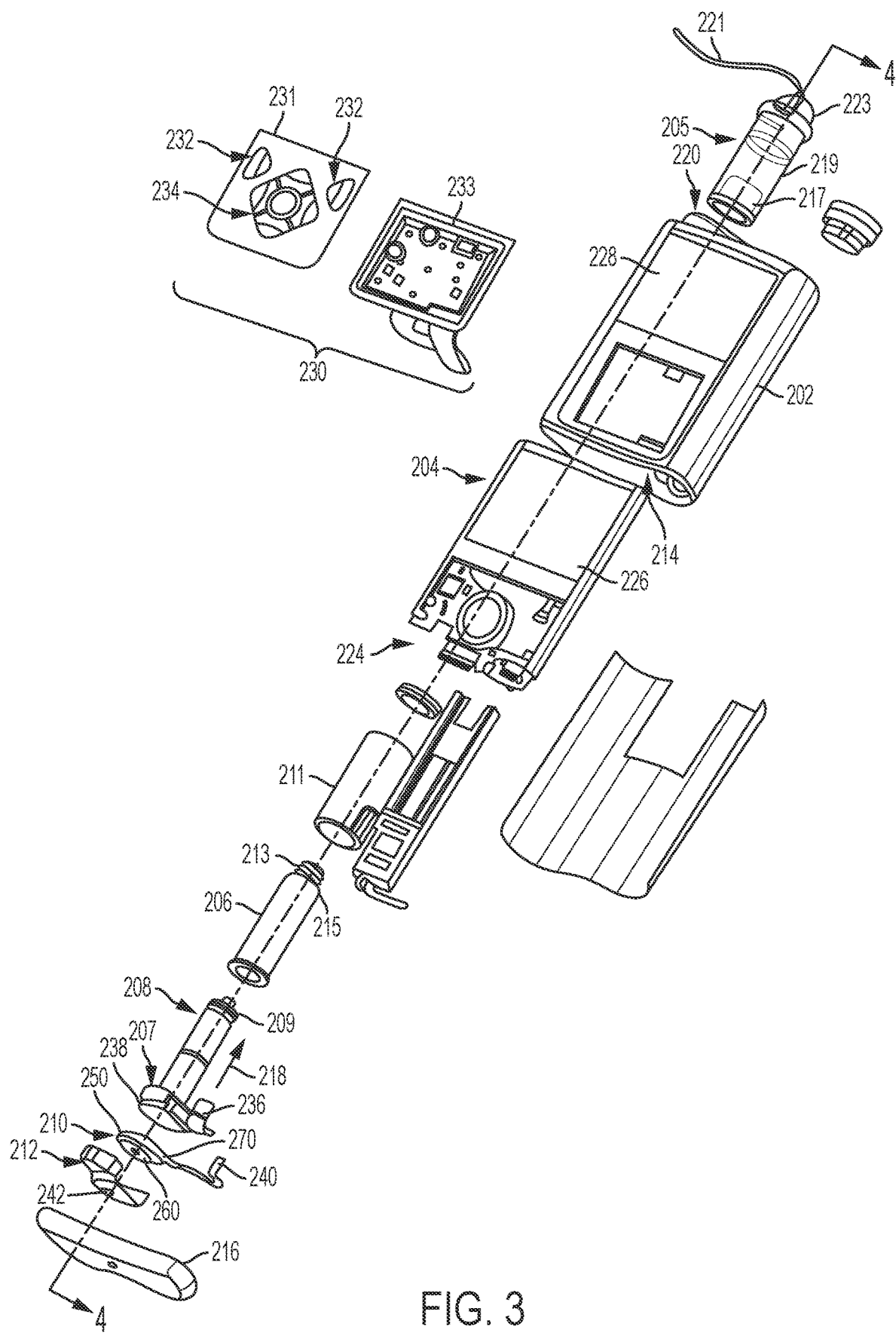
FIG. 3 is an exploded perspective view of the fluid infusion device of FIG. 2.
Figure 4:
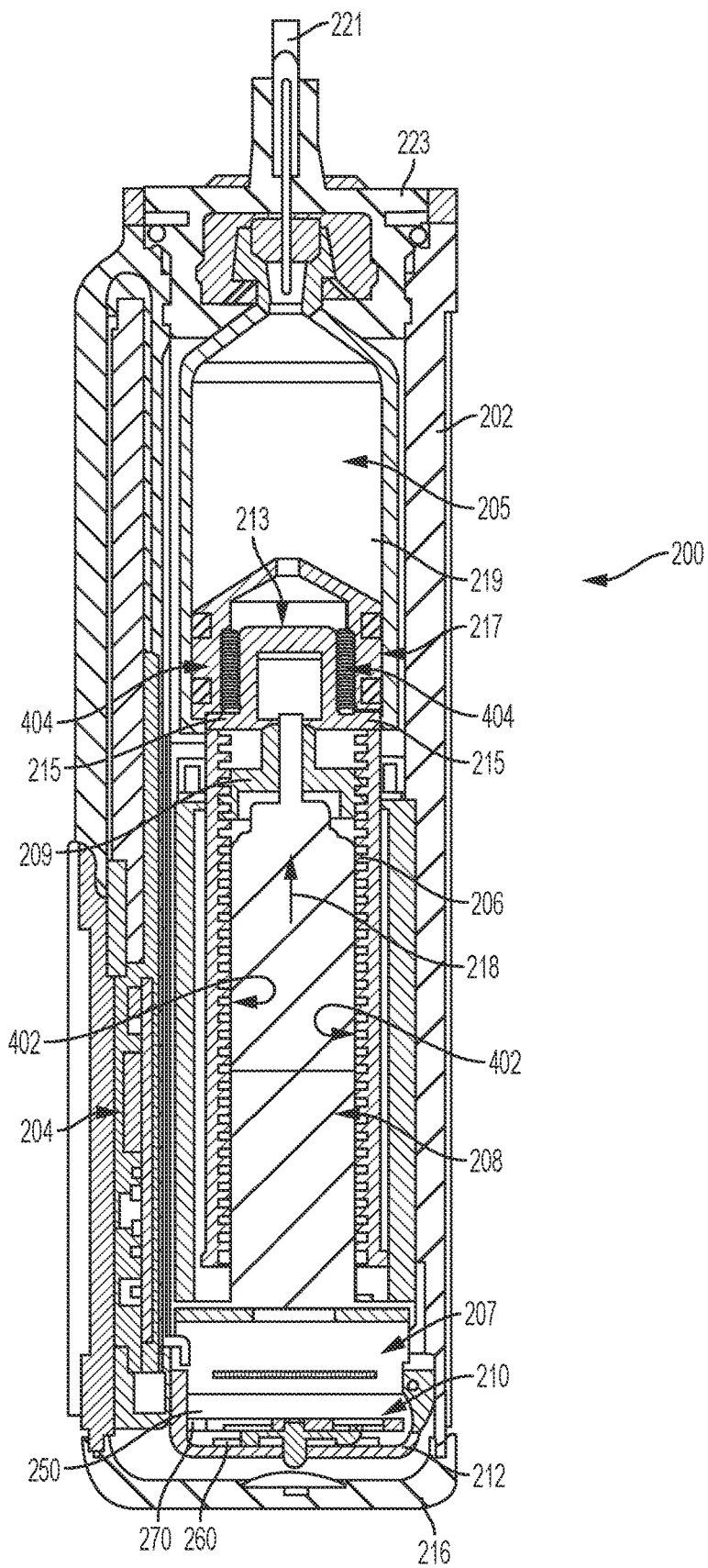
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion device 200 is subjected to shock or vibration; when the infusion device 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion device 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion device 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion device 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion device 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion device 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of the arrow that represents the axial direction 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
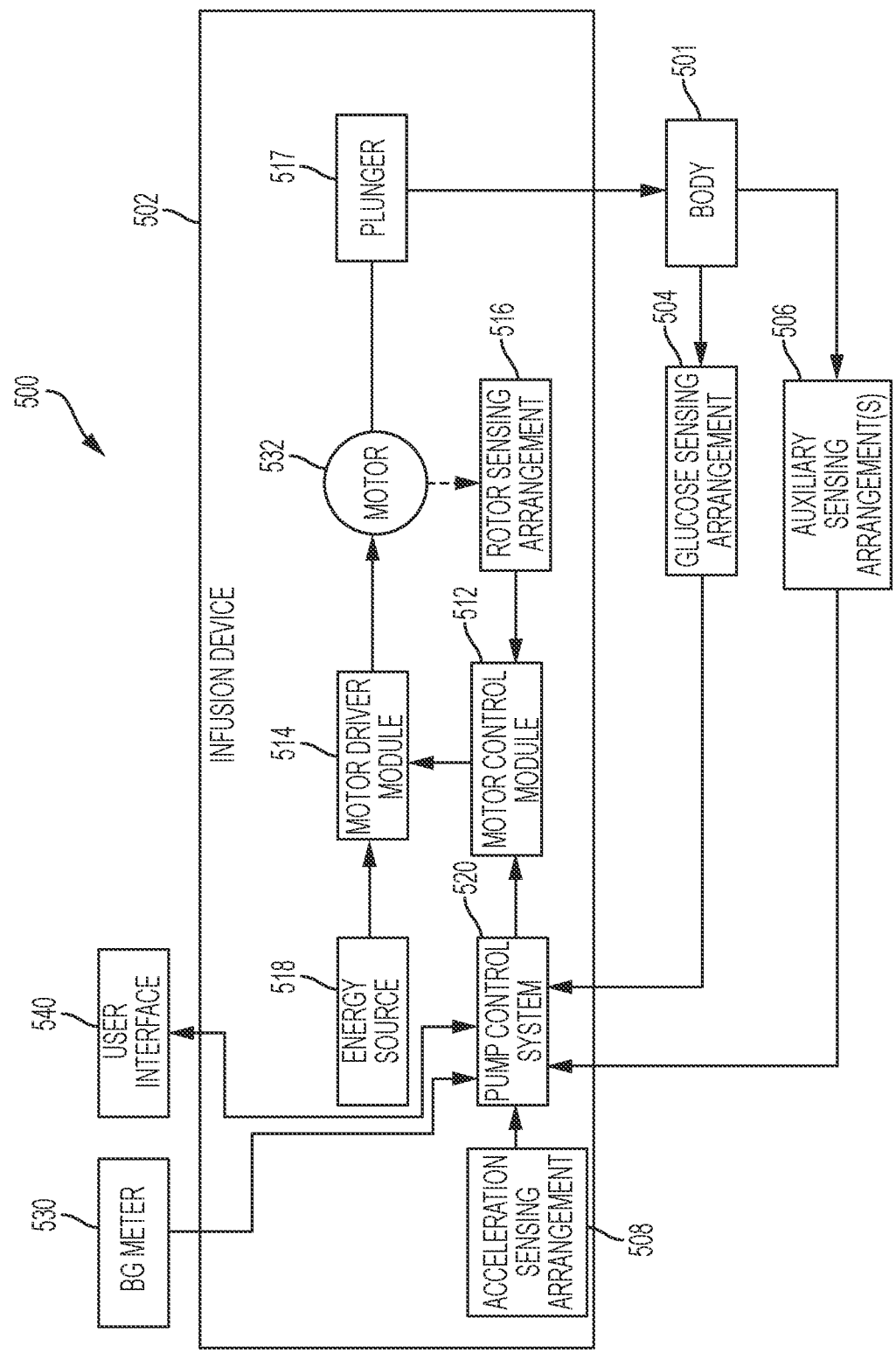
FIG. 5 is a block diagram of an exemplary infusion system suitable for use with a fluid infusion device in one or more embodiments.

FIG. 5 depicts an exemplary embodiment of an infusion system 500 suitable for use with an infusion device 502, such as any one of the infusion devices 102, 200 described above. The infusion system 500 is capable of controlling or otherwise regulating a physiological condition in the body 501 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., a blood glucose sensing arrangement 504) communicatively coupled to the infusion device 502. However, it should be noted that in alternative embodiments, the condition being regulated by the infusion system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the patient's glucose level, which is being regulated in the body 501 of the patient by the infusion system 500.

In exemplary embodiments, the sensing arrangement 504 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 501 of the patient. The output electrical signals are filtered or otherwise processed to obtain a measurement value indicative of the patient's interstitial fluid glucose level. In exemplary embodiments, a blood glucose meter 530, such as a finger stick device, is utilized to directly sense, detect, measure or otherwise quantify the blood glucose in the body 501 of the patient. In this regard, the blood glucose meter 530 outputs or otherwise provides a measured blood glucose value that may be utilized as a reference measurement for calibrating the sensing arrangement 504 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In exemplary embodiments, the infusion system 500 also includes one or more additional sensing arrangements 506, 508 configured to sense, detect, measure or otherwise quantify a characteristic of the body 501 of the patient that is indicative of a condition in the body 501 of the patient. In this regard, in addition to the glucose sensing arrangement 504, one or more auxiliary sensing arrangements 506 may be worn, carried, or otherwise associated with the body 501 of the patient to measure characteristics or conditions of the patient (or the patient's activity) that may influence the patient's glucose levels or insulin sensitivity. For example, a heart rate sensing arrangement 506 could be worn on or otherwise associated with the patient's body 501 to sense, detect, measure or otherwise quantify the patient's heart rate, which, in turn, may be indicative of exercise (and the intensity thereof) that is likely to influence the patient's glucose levels or insulin response in the body 501. In yet another embodiment, another invasive, interstitial, or subcutaneous sensing arrangement 506 may be inserted into the body 501 of the patient to obtain measurements of another physiological condition that may be indicative of exercise (and the intensity thereof), such as, for example, a lactate sensor, a ketone sensor, or the like. Depending on the embodiment, the auxiliary sensing arrangement(s) 506 could be realized as a standalone component worn by the patient, or alternatively, the auxiliary sensing arrangement(s) 506 may be integrated with the infusion device 502 or the glucose sensing arrangement 504.

The illustrated infusion system 500 also includes an acceleration sensing arrangement 508 (or accelerometer) that may be worn on or otherwise associated with the patient's body 501 to sense, detect, measure or otherwise quantify an acceleration of the patient's body 501, which, in turn, may be indicative of exercise or some other condition in the body 501 that is likely to influence the patient's insulin response. While the acceleration sensing arrangement 508 is depicted as being integrated into the infusion device 502 in FIG. 5, in alternative embodiments, the acceleration sensing arrangement 508 may be integrated with another sensing arrangement 504, 506 on the body 501 of the patient, or the acceleration sensing arrangement 508 may be realized as a separate standalone component that is worn by the patient.

In the illustrated embodiment, the pump control system 520 generally represents the electronics and other components of the infusion device 502 that control operation of the fluid infusion device 502 according to a desired infusion delivery program in a manner that is influenced by the sensed glucose value indicating the current glucose level in the body 501 of the patient. For example, to support a closed-loop operating mode, the pump control system 520 maintains, receives, or otherwise obtains a target or commanded glucose value, and automatically generates or otherwise determines dosage commands for operating an actuation arrangement, such as a motor 532, to displace the plunger 517 and deliver insulin to the body 501 of the patient based on the difference between the sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), insulin delivery limit(s), and/or other glucose threshold value(s) in a data storage element accessible to the pump control system 520. As described in greater detail, in one or more exemplary embodiments, the pump control system 520 automatically adjusts or adapts one or more parameters or other control information used to generate commands for operating the motor 532 in a manner that accounts for a likely change in the patient's glucose level or insulin response resulting from a meal, exercise, or other activity.

Still referring to FIG. 5, the target glucose value and other threshold glucose values utilized by the pump control system 520 may be received from an external component (e.g., CCD 106 and/or computing device 108) or be input by a patient via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the patient to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 532 (e.g., motor assembly 207) that is operable to displace a plunger 517 (e.g., plunger 217) in a reservoir (e.g., reservoir 205) and provide a desired amount of fluid to the body 501 of a patient. In this regard, displacement of the plunger 517 results in the delivery of a fluid, such as insulin, that is capable of influencing the patient's physiological condition to the body 501 of the patient via a fluid delivery path (e.g., via tubing 221 of an infusion set 225). A motor driver module 514 is coupled between an energy source 518 and the motor 532. The motor control module 512 is coupled to the motor driver module 514, and the motor control module 512 generates or otherwise provides command signals that operate the motor driver module 514 to provide current (or power) from the energy source 518 to the motor 532 to displace the plunger 517 in response to receiving, from a pump control system 520, a dosage command indicative of the desired amount of fluid to be delivered.

In exemplary embodiments, the energy source 518 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 518 into alternating electrical signals applied to respective phases of the stator windings of the motor 532 that result in current flowing through the stator windings that generates a stator magnetic field and causes the rotor of the motor 532 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 532 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 532 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 532 to achieve the desired delivery of fluid to the patient.

When the motor control module 512 is operating the motor driver module 514, current flows from the energy source 518 through the stator windings of the motor 532 to produce a stator magnetic field that interacts with the rotor magnetic field. In some embodiments, after the motor control module 512 operates the motor driver module 514 and/or motor 532 to achieve the commanded dosage, the motor control module 512 ceases operating the motor driver module 514 and/or motor 532 until a subsequent dosage command is received. In this regard, the motor driver module 514 and the motor 532 enter an idle state during which the motor driver module 514 effectively disconnects or isolates the stator windings of the motor 532 from the energy source 518. In other words, current does not flow from the energy source 518 through the stator windings of the motor 532 when the motor 532 is idle, and thus, the motor 532 does not consume power from the energy source 518 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 502, while in alternative embodiments, the pump control system 520 may be implemented by a remote computing device that is physically distinct and/or separate from the infusion device 502, such as, for example, the CCD 106 or the computing device 108.

Figure 6:
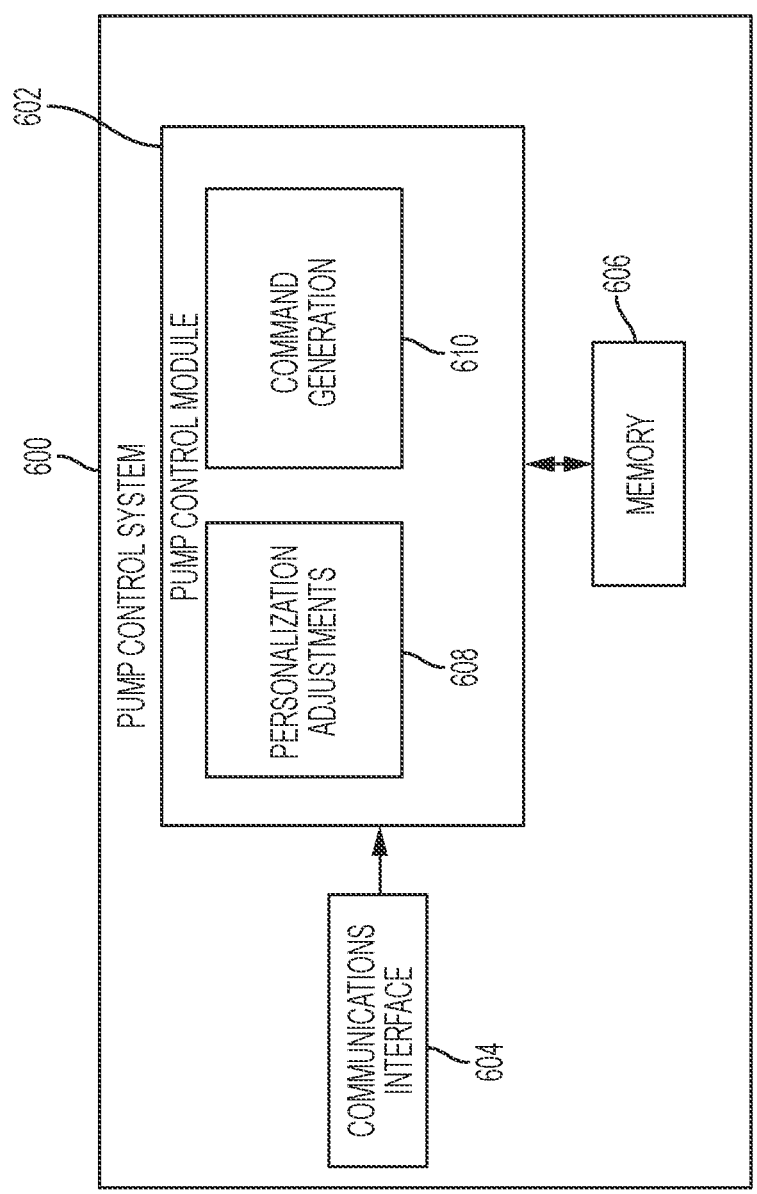
FIG. 6 is a block diagram of an exemplary pump control system suitable for use in the infusion device in the infusion system of FIG. 5 in one or more embodiments.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In various embodiments, the pump control module 602 is also coupled to one or more user interface elements (e.g., user interface 230, 540) for receiving user inputs (e.g., target glucose values or other glucose thresholds) and providing notifications, alerts, or other therapy information to the patient.

The communications interface 604 generally represents the hardware, circuitry, logic, firmware and/or other components of the pump control system 600 that are coupled to the pump control module 602 and configured to support communications between the pump control system 600 and the various sensing arrangements 504, 506, 508. In this regard, the communications interface 604 may include or otherwise be coupled to one or more transceiver modules capable of supporting wireless communications between the pump control system 520, 600 and the sensing arrangement 504, 506, 508. For example, the communications interface 604 may be utilized to receive sensor measurement values or other measurement data from each sensing arrangement 504, 506, 508 in an infusion system 500. In other embodiments, the communications interface 604 may be configured to support wired communications to/from the sensing arrangement(s) 504, 506, 508. In various embodiments, the communications interface 604 may also support communications with another electronic device (e.g., CCD 106 and/or computer 108) in an infusion system (e.g., to upload sensor measurement values to a server or other computing device, receive control information from a server or other computing device, and the like).

The pump control module 602 generally represents the hardware, circuitry, logic, firmware and/or other component of the pump control system 600 that is coupled to the communications interface 604 and configured to determine dosage commands for operating the motor 532 to deliver fluid to the body 501 based on measurement data received from the sensing arrangements 504, 506, 508 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 532 of the infusion device 502 in an autonomous operating mode based at least in part on a current measurement value for a condition in the body 501 of the patient. For example, in a closed-loop operating mode, the command generation application 610 may determine a dosage command for operating the motor 532 to deliver insulin to the body 501 of the patient based at least in part on the current glucose measurement value most recently received from the sensing arrangement 504 to regulate the patient's blood glucose level to a target reference glucose value. Additionally, the command generation application 610 may generate dosage commands for boluses that are manually-initiated or otherwise instructed by a patient via a user interface element.

In exemplary embodiments, the pump control module 602 also implements or otherwise executes a personalization application 608 that is cooperatively configured to interact with the command generation application 610 to support adjusting dosage commands or control information dictating the manner in which dosage commands are generated in a personalized, patient-specific manner. In this regard, in some embodiments, based on correlations between current or recent measurement data and the current operational context relative to historical data associated with the patient, the personalization application 608 may adjust or otherwise modify values for one or more parameters utilized by the command generation application 610 when determining dosage commands, for example, by modifying a parameter value at a register or location in memory 606 referenced by the command generation application 610. In yet other embodiments, the personalization application 608 may predict meals or other events or activities that are likely to be engaged in by the patient and output or otherwise provide an indication of the predicted patient behavior for confirmation or modification by the patient, which, in turn, may then be utilized to adjust the manner in which dosage commands are generated to regulate glucose in a manner that accounts for the patient's behavior in a personalized manner.

Still referring to FIG. 6, depending on the embodiment, the pump control module 602 may be implemented or realized with at least one general purpose processor device, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 608, 610 and perform tasks, operations, functions, and processes described herein.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
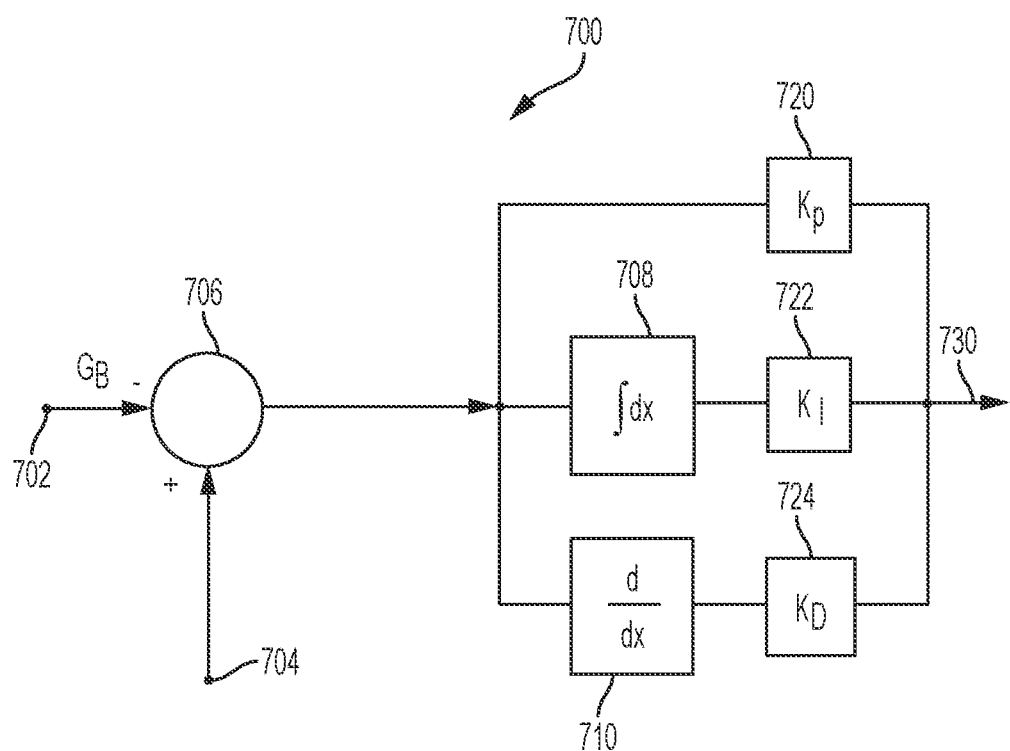
FIG. 7 is a block diagram of a closed-loop control system that may be implemented or otherwise supported by the pump control system in the fluid infusion device of FIGS. 5-6 in one or more exemplary embodiments.

FIG. 7 depicts an exemplary closed-loop control system 700 that may be implemented by a pump control system 520, 600 to provide a closed-loop operating mode that autonomously regulates a condition in the body of a patient to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 532 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 532 to deliver insulin to the body of the patient to influence the patient's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determining gain coefficients are described in greater detail in U.S. Pat. No. 7,402,153, which is incorporated by reference.

In one or more exemplary embodiments, the PID gain coefficients are patient-specific and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

In one or more exemplary embodiments, one or more parameters of the closed-loop control system 700 are automatically adjusted or adapted in a personalized manner to account for potential changes in the patient's glucose level or insulin sensitivity resulting from meals, exercise, or other events or activities. For example, in one or more embodiments, the target glucose value may be decreased in advance of a predicted meal event to achieve an increase in the insulin infusion rate to effectively pre-bolus a meal, and thereby reduce the likelihood of postprandial hyperglycemia. Additionally or alternatively, the time constant or gain coefficient associated with one or more paths of the closed-loop control system 700 may be adjusted to tune the responsiveness to deviations between the measured glucose value and the target glucose value. For example, based on the particular type of meal being consumed or the particular time of day during which the meal is consumed, the time constant associated with the derivative block 710 or derivative term path may be adjusted to make the closed-loop control more or less aggressive in response to an increase in the patient's glucose level based on the patient's historical glycemic response to the particular type of meal.

Figure 8:
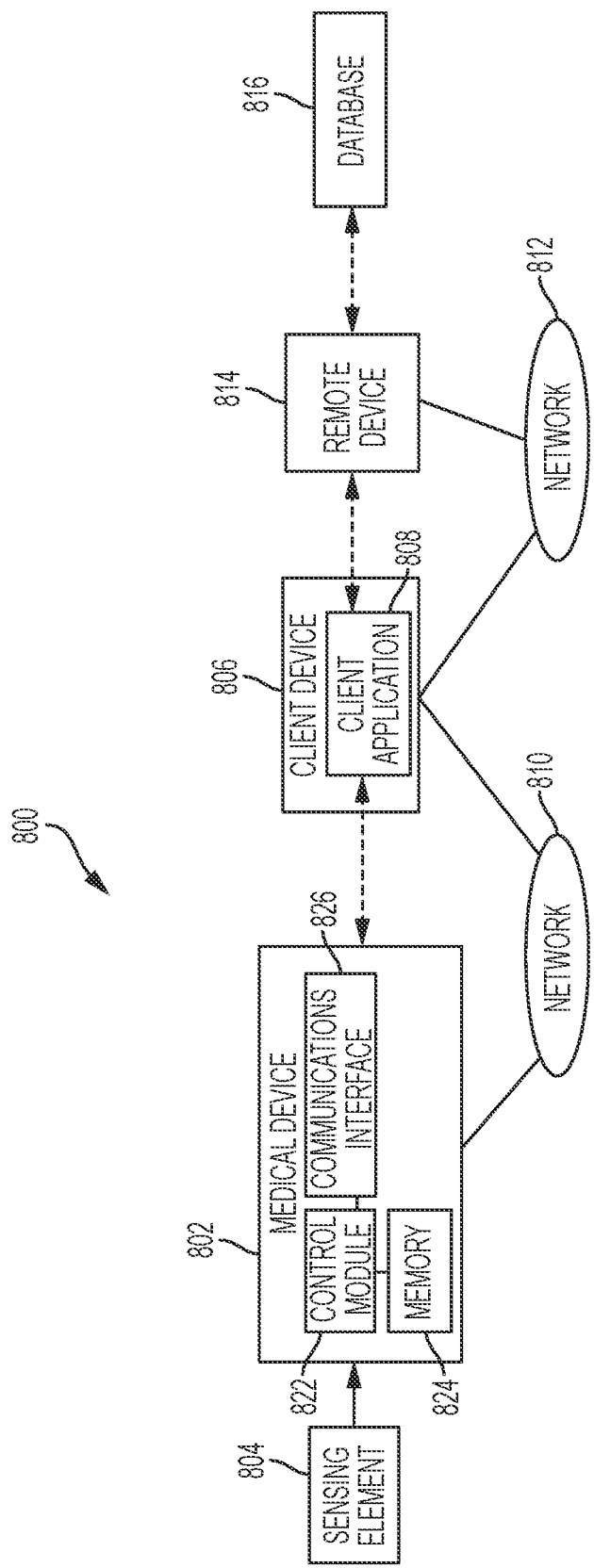
FIG. 8 is a block diagram of an exemplary patient monitoring system.

FIG. 8 depicts an exemplary embodiment of a patient monitoring system 800. The patient monitoring system 800 includes a medical device 802 that is communicatively coupled to a sensing element 804 that is inserted into the body of a patient or otherwise worn by the patient to obtain measurement data indicative of a physiological condition in the body of the patient, such as a sensed glucose level. The medical device 802 is communicatively coupled to a client device 806 via a communications network 810, with the client device 806 being communicatively coupled to a remote device 814 via another communications network 812. In this regard, the client device 806 may function as an intermediary for uploading or otherwise providing measurement data from the medical device 802 to the remote device 814. It should be appreciated that FIG. 8 depicts a simplified representation of a patient monitoring system 800 for purposes of explanation and is not intended to limit the subject matter described herein in any way.

In exemplary embodiments, the client device 806 is realized as a mobile phone, a smartphone, a tablet computer, or other similar mobile electronic device; however, in other embodiments, the client device 806 may be realized as any sort of electronic device capable of communicating with the medical device 802 via network 810, such as a laptop or notebook computer, a desktop computer, or the like. In exemplary embodiments, the network 810 is realized as a Bluetooth network, a ZigBee network, or another suitable personal area network. That said, in other embodiments, the network 810 could be realized as a wireless ad hoc network, a wireless local area network (WLAN), or local area network (LAN). The client device 806 includes or is coupled to a display device, such as a monitor, screen, or another conventional electronic display, capable of graphically presenting data and/or information pertaining to the physiological condition of the patient. The client device 806 also includes or is otherwise associated with a user input device, such as a keyboard, a mouse, a touchscreen, or the like, capable of receiving input data and/or other information from the user of the client device 806.

In exemplary embodiments, a user, such as the patient, the patient's doctor or another healthcare provider, or the like, manipulates the client device 806 to execute a client application 808 that supports communicating with the medical device 802 via the network 810. In this regard, the client application 808 supports establishing a communications session with the medical device 802 on the network 810 and receiving data and/or information from the medical device 802 via the communications session. The medical device 802 may similarly execute or otherwise implement a corresponding application or process that supports establishing the communications session with the client application 808. The client application 808 generally represents a software module or another feature that is generated or otherwise implemented by the client device 806 to support the processes described herein. Accordingly, the client device 806 generally includes a processing system and a data storage element (or memory) capable of storing programming instructions for execution by the processing system, that, when read and executed, cause processing system to create, generate, or otherwise facilitate the client application 808 and perform or otherwise support the processes, tasks, operations, and/or functions described herein. Depending on the embodiment, the processing system may be implemented using any suitable processing system and/or device, such as, for example, one or more processor devices, central processing units (CPUs), controllers, microprocessors, microcontrollers, processing cores and/or other hardware computing resources configured to support the operation of the processing system described herein. Similarly, the data storage element or memory may be realized as a random-access memory (RAM), read only memory (ROM), flash memory, magnetic or optical mass storage, or any other suitable non-transitory short or long-term data storage or other computer-readable media, and/or any suitable combination thereof.

In one or more embodiments, the client device 806 and the medical device 802 establish an association (or pairing) with one another over the network 810 to support subsequently establishing a point-to-point or peer-to-peer communications session between the medical device 802 and the client device 806 via the network 810. For example, in accordance with one embodiment, the network 810 is realized as a Bluetooth network, wherein the medical device 802 and the client device 806 are paired with one another (e.g., by obtaining and storing network identification information for one another) by performing a discovery procedure or another suitable pairing procedure. The pairing information obtained during the discovery procedure allows either of the medical device 802 or the client device 806 to initiate the establishment of a secure communications session via the network 810.

In one or more exemplary embodiments, the client application 808 is also configured to store or otherwise maintain an address and/or other identification information for the remote device 814 on the second network 812. In this regard, the second network 812 may be physically and/or logically distinct from the network 810, such as, for example, the Internet, a cellular network, a wide area network (WAN), or the like. The remote device 814 generally represents a server or other computing device configured to receive and analyze or otherwise monitor measurement data, event log data, and potentially other information obtained for the patient associated with the medical device 802. In exemplary embodiments, the remote device 814 is coupled to a database 816 configured to store or otherwise maintain data associated with individual patients. In practice, the remote device 814 may reside at a location that is physically distinct and/or separate from the medical device 802 and the client device 806, such as, for example, at a facility that is owned and/or operated by or otherwise affiliated with a manufacturer of the medical device 802. For purposes of explanation, but without limitation, the remote device 814 may alternatively be referred to herein as a server.

Still referring to FIG. 8, the sensing element 804 generally represents the component of the patient monitoring system 800 that is configured to generate, produce, or otherwise output one or more electrical signals indicative of a physiological condition that is sensed, measured, or otherwise quantified by the sensing element 804. In this regard, the physiological condition of a patient influences a characteristic of the electrical signal output by the sensing element 804, such that the characteristic of the output signal corresponds to or is otherwise correlative to the physiological condition that the sensing element 804 is sensitive to. In exemplary embodiments, the sensing element 804 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 804.

The medical device 802 generally represents the component of the patient monitoring system 800 that is communicatively coupled to the output of the sensing element 804 to receive or otherwise obtain the measurement data samples from the sensing element 804 (e.g., the measured glucose and characteristic impedance values), store or otherwise maintain the measurement data samples, and upload or otherwise transmit the measurement data to the remote device 814 or server via the client device 806. In one or more embodiments, the medical device 802 is realized as an infusion device 102, 200, 502 configured to deliver a fluid, such as insulin, to the body of the patient. That said, in other embodiments, the medical device 802 could be a standalone sensing or monitoring device separate and independent from an infusion device (e.g., sensing arrangement 104, 504). It should be noted that although FIG. 8 depicts the medical device 802 and the sensing element 804 as separate components, in practice, the medical device 802 and the sensing element 804 may be integrated or otherwise combined to provide a unitary device that can be worn by the patient.

In exemplary embodiments, the medical device 802 includes a control module 822, a data storage element 824 (or memory), and a communications interface 826. The control module 822 generally represents the hardware, circuitry, logic, firmware and/or other component(s) of the medical device 802 that is coupled to the sensing element 804 to receive the electrical signals output by the sensing element 804 and perform or otherwise support various additional tasks, operations, functions and/or processes described herein. Depending on the embodiment, the control module 822 may be implemented or realized with a general purpose processor device, a microprocessor device, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 822 includes an analog-to-digital converter (ADC) or another similar sampling arrangement that samples or otherwise converts an output electrical signal received from the sensing element 804 into corresponding digital measurement data value. In other embodiments, the sensing element 804 may incorporate an ADC and output a digital measurement value.

The communications interface 826 generally represents the hardware, circuitry, logic, firmware and/or other components of the medical device 802 that are coupled to the control module 822 for outputting data and/or information from/to the medical device 802 to/from the client device 806. For example, the communications interface 826 may include or otherwise be coupled to one or more transceiver modules capable of supporting wireless communications between the medical device 802 and the client device 806. In exemplary embodiments, the communications interface 826 is realized as a Bluetooth transceiver or adapter configured to support Bluetooth Low Energy (BLE) communications.

In exemplary embodiments, the remote device 814 receives, from the client device 806, measurement data values associated with a particular patient (e.g., sensor glucose measurements, acceleration measurements, and the like) that were obtained using the sensing element 804, and the remote device 814 stores or otherwise maintains the historical measurement data in the database 816 in association with the patient (e.g., using one or more unique patient identifiers). Additionally, the remote device 814 may also receive, from or via the client device 806, meal data or other event log data that may be input or otherwise provided by the patient (e.g., via client application 808) and store or otherwise maintain historical meal data and other historical event or activity data associated with the patient in the database 816. In this regard, the meal data include, for example, a time or timestamp associated with a particular meal event, a meal type or other information indicative of the content or nutritional characteristics of the meal, and an indication of the size associated with the meal. In exemplary embodiments, the remote device 814 also receives historical fluid delivery data corresponding to basal or bolus dosages of fluid delivered to the patient by an infusion device 102, 200, 502. For example, the client application 808 may communicate with an infusion device 102, 200, 502 to obtain insulin delivery dosage amounts and corresponding timestamps from the infusion device 102, 200, 502, and then upload the insulin delivery data to the remote device 814 for storage in association with the particular patient. The remote device 814 may also receive geolocation data and potentially other contextual data associated with a device 802, 806 from the client device 806 and/or client application 808, and store or otherwise maintain the historical operational context data in association with the particular patient. In this regard, one or more of the devices 802, 806 may include a global positioning system (GPS) receiver or similar modules, components or circuitry capable of outputting or otherwise providing data characterizing the geographic location of the respective device 802, 806 in real-time.

The historical patient data may be analyzed by one or more of the remote device 814, the client device 806, and/or the medical device 802 to alter or adjust operation of an infusion device 102, 200, 502 to influence fluid delivery in a personalized manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200, 502 that control or regulate insulin delivery may then be modified or adjusted to proactively account for the patient's likely meal activity and glycemic response.

In one or more exemplary embodiments, the remote device 814 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other patients. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 814 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

An insulin infusion device of the type described above can be suitably configured to calculate an upper limit on the insulin delivery rate that can be used during an automatic basal insulin delivery mode. In such an automatic mode, the infusion device automatically delivers insulin (at a rate that is less than or equal to the calculated upper limit). This upper limit, Umax, can be dynamically adjusted to better suit the needs of the user. For example, an exemplary embodiment of the infusion device adapts Umax once a day, e.g., at midnight. In addition to the basal insulin that is automatically provided by the infusion device, the user (or a caregiver) can also issue additional insulin boluses by announcing (entering) a carbohydrate value for a meal and/or by entering a blood glucose meter reading.

If the insulin infusion device is already delivering insulin at the Umax rate (the upper limit) while in the automatic basal insulin mode, then it can be assumed that the patient needs additional insulin to better regulate blood glucose levels. To this end, the infusion device can respond to such a condition by considering whether a correction bolus is needed. In certain embodiments, when the automated insulin delivery rate exceeds a specified rate for at least a designated period of time, then the infusion device reacts by initiating an automated correction bolus procedure to calculate and possibly deliver a correction bolus. If the calculated correction bolus is above a baseline threshold amount and is determined to be safe to administer, then the infusion device issues the correction bolus as a supplement to the basal insulin that is already being delivered. As one non-limiting example, if the automatic basal insulin rate has been above a specified percentage of Umax (e.g., 90%, 92.5%, etc.) for at least one hour, then the insulin infusion device will proceed with the automated correction bolus procedure. As another non-limiting example, if the automatic basal insulin rate reaches Umax at any time, then the automated correction bolus procedure will be triggered. These and other triggering conditions and mechanisms can be employed in an exemplary embodiment of the insulin infusion device.

In accordance with the embodiments presented here, the initial (potential) correction bolus is calculated as follows:

$$\text{Correction Bolus} = \frac{BG - \text{Target}}{ISF} - IOB \quad \text{(Equation 1)}$$

In this expression:

BG is a blood glucose measurement for the user;

Target is the desired blood glucose level for the user (which is user-adjustable in the manual delivery mode, and is fixed during the automatic mode);

ISF is the user's Insulin Sensitivity Factor (which is user-adjustable in the manual delivery mode, and is determined according to $$\frac{1800}{\text{Total Daily Insulin Dose}}$$

during the automatic mode); and

IOB is the current Insulin On Board, or active insulin, that is determined by accounting for all bolus insulin deliveries, and by reducing the amount over time according to the user setting for active insulin time. For this example, the total daily insulin dose is a median value that is calculated based on two to six days of the patient's total daily dose.

The initial correction bolus can be scaled by a multiplier that has a value between 0.0 and 1.0 to reduce the bolus amount as needed. More specifically, the infusion device intelligently scales the initial correction bolus amount (or withholds the bolus) to prevent the risk of hypoglycemia following delivery of the correction bolus.

In accordance with certain embodiments, the insulin infusion device performs a correction bolus check during the automatic mode under the following conditions: a BG value (e.g., a BG meter reading or a glucose sensor reading) is entered into the device or is otherwise obtained by the device; the BG value is greater than a threshold value, such as 150 mg/dL or 120 mg/dL; and the calculated correction bolus value is greater than zero after deducting active insulin and applying safe correction bolus logic. If all of these conditions are met, then the infusion device provides a message recommending a correction bolus to the user. The user may decide to either accept the correction bolus or reject it.

As mentioned above, the baseline initial correction bolus value can be scaled, based on a safe correction bolus methodology utilized by the infusion device. The safe correction bolus methodology incorporates a prediction model to estimate whether the correction bolus is likely to lower the user's BG level below a stated low glucose threshold (such as 80 mg/dL) in the near future (such as within the next two to four hours). If the BG level is predicted to go below the low glucose threshold value, then the initial correction bolus value is incrementally reduced until the predicted level remains above the threshold value.

The improved methodology described here delivers correction boluses automatically without any user input or acknowledgement. The core computation of the automatic correction bolus is based on Equation 1 set forth above. However, the correction target is lowered from a default, standard, or typical value to a reduced value, such as 120 mg/dL. Moreover, correction boluses do not require BG meter readings; they can be computed based on readings from a patient-worn continuous glucose sensor. That said, if a valid BG meter value is available, then that value will be preferred.

Figure 9:
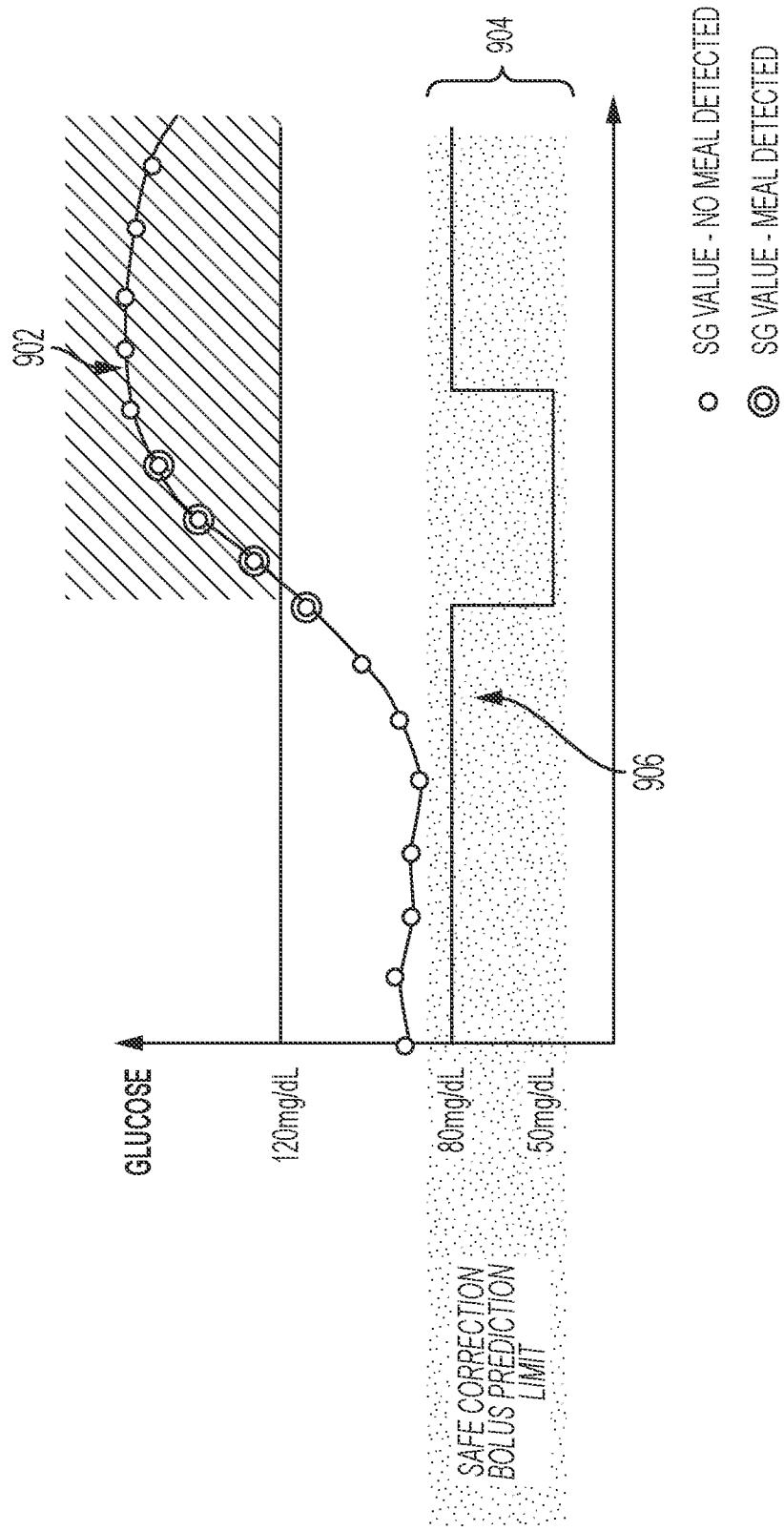
FIG. 9 is a diagram that illustrates a scenario where an automatic correction bolus can be delivered.

A meal detection algorithm is also utilized in the exemplary embodiment of the insulin infusion device. In this regard, FIG. 9 is a diagram that illustrates a scenario where an automatic correction bolus can be delivered. The vertical axis indicates BG measurements, and the horizontal axis represents time. FIG. 9 includes a plot 902 of BG values, and an indication of the lowered correction target of 120 mg/dL. For this particular implementation, the BG values are actual (measured) values, although predicted values could also be used in certain applications. FIG. 9 also depicts a zone 904 that identifies low BG thresholds that are used for comparison against predicted BG values in the manner described in more detail below. The BG limits for this particular example are 80 mg/dL and 50 mg/dL. In practice, different default and reduced BG limits (which may be fixed or dynamically adjustable) may be employed as desired for the given implementation.

The meal detection algorithm calculates the rate of change (slope) defined by previous sensor glucose readings (e.g., the last three to seven readings) to detect a post-prandial rise based on the direction, magnitude, and duration of the slopes. The four circled points of the plot 902 depict an instance of such a rise in measured BG values. If a meal is detected in this manner by the algorithm, then the low prediction threshold used in the safe correction bolus algorithm will be temporarily lowered from 80 mg/dL to 50 mg/dL. The timing of this reduction is depicted in FIG. 9, where the plot 906 indicates the value of the low prediction threshold (also referred to herein as the low BG threshold level) over time. As the plot 906 indicates, the low prediction threshold remains at its default value of 80 mg/dL unless the measured BG values exhibit a rising trend that is typically associated with consumption of a meal. If a meal is detected, the low prediction threshold is adjusted downward to 50 mg/dL. As a result of this low glucose threshold reduction, the safe correction bolus algorithm deducts less from a calculated correction bolus (if there is a detected pattern of sustained rising rate of change of sensed glucose values at the time of the correction bolus). That said, the final correction bolus amount will not exceed the initially calculated value (as computed by Equation 1).

For this particular embodiment, the automatic correction bolus algorithm computes a possible correction bolus amount with each new BG measurement that is obtained, and delivers the calculated correction bolus if the following conditions are met: (1) the automatic basal insulin delivery is currently at the maximum allowable rate of Umax; (2) the intended correction bolus amount is greater than 10% of the Umax level; and (3) the automatic delivery mode is neither operating in the Safe Basal mode nor the Temporary Glucose Target mode.

In general, automatic correction boluses will be relatively small and will occur during periods of positive rates of glucose change when BG values are rising above 120 mg/dL. For example, assume that the previous BG value was 120 mg/dL, the user's BG is rising rapidly at a rate of 2.0 mg/dL/min, the automatic basal delivery is at Umax, and there is no insulin on board from a prior bolus. If a new BG value of 130 mg/dL is received (for example, sensor glucose values are received every five minutes in the exemplary system described here), an automatic correction bolus would be delivered based on the 10 mg/dL difference between the current BG value of 130 mg/dL and the correction target value of 120 mg/dL. Note that for this example, the first automatic correction bolus must exceed Umax by at least 10% for it to be delivered. Accordingly, it is not obvious at what level of glucose the first correction bolus will be implemented.

Continuing this example, if glucose continues to rise at the same rate and the next BG value of 140 mg/dL is received five minutes later, then another correction bolus would be calculated based on the 20 mg/dL difference between the current BG value and the correction target, and the infusion device would deduct the active insulin from the prior correction bolus. Therefore, the new correction bolus would effectively only account for the 10 mg/dL difference between the current BG value and the previous BG value instead of the 20 mg/dL difference between the current BG value and the correction target. If the user's BG then stabilized at 140 mg/dL and a new BG value is received, then the insulin on board deduction from the previous two corrections would counter the correction calculation based on the 20 mg/dL difference between the BG and the correction target, so no additional correction would be given.

The benefits of automating the correction bolus will help to provide more effective therapy while reducing the burden on the user to manage their diabetes. There are multiple safeguards in place to prevent over-delivery of insulin by the automatic correction bolus feature. These safeguards include the following, without limitation:

The correction bolus target is fixed at 120 mg/dL, which provides a margin against hypoglycemia.

Safety of each correction bolus is checked by predicting BG two hours in the future with the help of a mathematical model. If hypoglycemia is predicted, the safeguard can reduce the size of the correction bolus (up to zero) until no hypoglycemia is predicted.

In certain embodiments, automatic correction boluses are suppressed when the total amount of correction bolus commands in a 45-minute moving window exceeds 8% of the total daily dose. Correction boluses resume when the total amount of correction bolus commands within the 45-minute window does not exceed 1% of total daily dose.

In certain embodiments, sensor glucose values that may be used for correction boluses are limited to 250 mg/dL when a new sensor is less than 12 hours old and the calibration factor is greater than 8 mg/dL/nA.

In certain embodiments, automatic correction boluses are suppressed when a sensor glucose spike is detected that is greater than 65 mg/dL/5 minutes (if a sensor glucose measurement is available) or 125 mg/dL/5 minutes (based on the current ISIG and calibration factor when a sensor glucose measurement is not available), and the associated ISIG spike is greater than 15 nA/5 minutes. Correction boluses may resume following a blood glucose entry with successful calibration factor.

Automatic correction bolus is delivered after deducting insulin on board. The duration of active insulin on board can be adjusted by the user (minimum two hours, maximum eight hours).

The insulin sensitivity factor, ISF, used in the automatic correction bolus calculation is adapted to the user's physiology based on total daily dose instead of an adjustable user setting. Accordingly, the user may not use the ISF setting to adjust the size of automatic correction boluses.

A prolonged high alert occurs if measured sensor glucose stays above 250 mg/dL for three hours.

The continuous glucose sensor is calibrated at least once every 12 hours by an independent fingerstick (or other blood sample) BG measurement.

All BG meter measurements that are entered into the insulin infusion device (either manually or through a linked meter) and confirmed by the user are used for a sensor integrity check and to calibrate the continuous glucose sensor.

Figure 10:
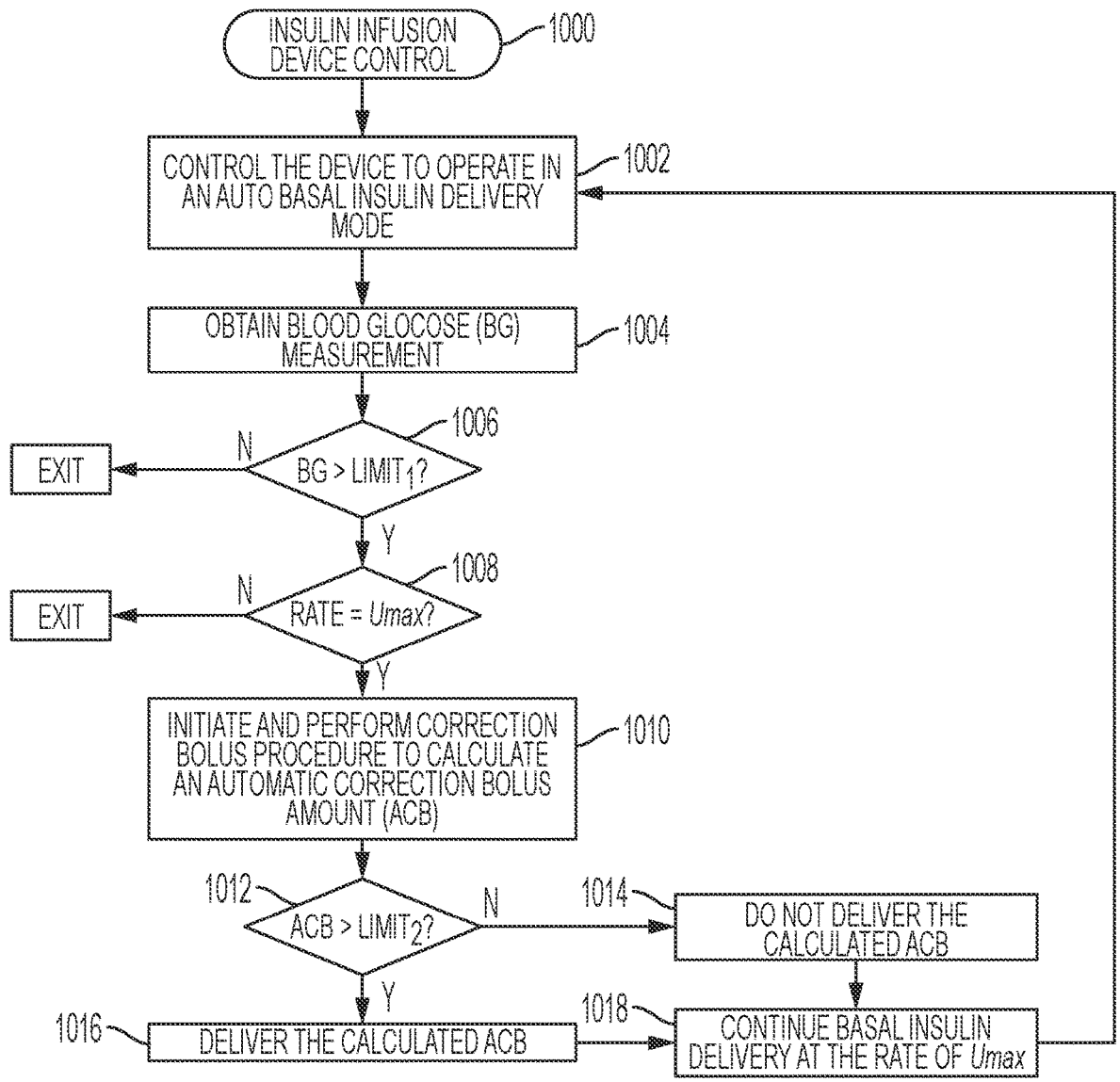
FIG. 10 is a flow diagram that illustrates an exemplary embodiment of a process for controlling the operation of an insulin infusion device.

FIG. 10 is a flow diagram that illustrates an exemplary embodiment of an insulin infusion device control process 1000. The process 1000 is suitable for controlling the operation of an infusion device of the type described above with reference to FIGS. 1-8, namely, an infusion device having a fluid reservoir for insulin to be delivered from the device to the body of a user, and having at least one processor device that executes computer-readable instructions to carry out the process 1000. The various tasks performed in connection with a process described herein may be performed by software, hardware, firmware, or any combination thereof. For illustrative purposes, a description of a process may refer to elements mentioned above in connection with FIGS. 1-8. It should be appreciated that a described process may include any number of additional or alternative tasks, the tasks shown in the figures need not be performed in the illustrated order, and an illustrated process may be incorporated into a more comprehensive procedure or process having additional functionality not described in detail herein. Moreover, one or more of the tasks shown for an illustrated process could be omitted from an embodiment of the process as long as the intended overall functionality remains intact.

The process 1000 represents one iteration that is performed for a current sampling point or period of time, which corresponds to the most recent sampling period. This example assumes that the insulin infusion device is already being controlled to operate in an automatic basal insulin delivery mode (task 1002) that delivers basal insulin to the body of the user. This example also assumes that the process 1000 receives relevant data in accordance with a predetermined schedule (e.g., a sampling period of five minutes). Accordingly, the process 1000 receives, obtains, or accesses information that may have an influence on the manner in which the infusion device delivers insulin to the user. For example, the process 1000 obtains a current or most recent BG measurement that indicates a current BG level of the user (task 1004). As mentioned above, the BG measurement can be obtained from a BG meter (typically a fingerstick measurement) or a continuous glucose sensor that is coupled to the body of the user.

For this particular embodiment, the correction bolus procedure is initiated when two conditions are satisfied: (1) the current BG measurement exceeds a correction bolus threshold value; and (2) a maximum allowable basal insulin infusion rate (Umax) has been reached during operation in the automatic basal insulin delivery mode. To this end, the process 1000 checks whether the obtained BG measurement is greater than the correction bolus threshold value, $LIMIT_1$, (query task 1006) and whether the current basal insulin infusion rate equals Umax (query task 1008). For this non-limiting example, the correction bolus threshold value ($LIMIT_1$) is 120 mg/dL and Umax will typically fall within the range of about 0.5 to about 3.0 Units/hour (the actual value checked at query task 1008 is patient-specific). If either of these conditions are not met, then the process 1000 exits without considering an automatic correction bolus. If both of these conditions are satisfied, however, then the process 1000 continues by initiating and performing the correction bolus procedure to calculate an automatic correction bolus amount (task 1010). The manner in which the automatic correction bolus (ACB) amount is calculated will be described in more detail below with reference to FIG. 11. In certain implementations, an initial or proposed ACB amount is calculated and scaled or adjusted as needed to arrive at a final ACB amount.

The illustrated embodiment of the process 1000 performs an additional check before delivering a correction bolus. More specifically, the process 1000 checks whether the computed final ACB amount exceeds a bolus delivery threshold amount, $LIMIT_2$ (query task 1012). If the final ACB amount does not exceed the bolus delivery threshold amount (the "No" branch of query task 1012), then the insulin infusion device is controlled such that the calculated final ACB amount is not delivered to the user (task 1014). If the final ACB amount exceeds the bolus delivery threshold amount (the "Yes" branch of query task 1012), then the insulin infusion device is controlled to deliver the calculated final ACB amount to the user (task 1016). In other words, the final ACB amount is delivered only when it exceeds the bolus delivery threshold amount, which may be defined as a percentage of Umax, e.g., ten percent of the current value of Umax. The bolus delivery threshold amount is utilized in the exemplary embodiment to avoid delivery of small insulin boluses, which may have little effect and/or be unnecessary. Whether or not the final ACB amount is delivered, the process 1000 continues by delivering basal insulin at the rate of Umax for at least the next cycle or sampling period (task 1018). As depicted in FIG. 10, the process 1000 leads back to task 1002 to repeat itself for the next iteration.

Figure 11:
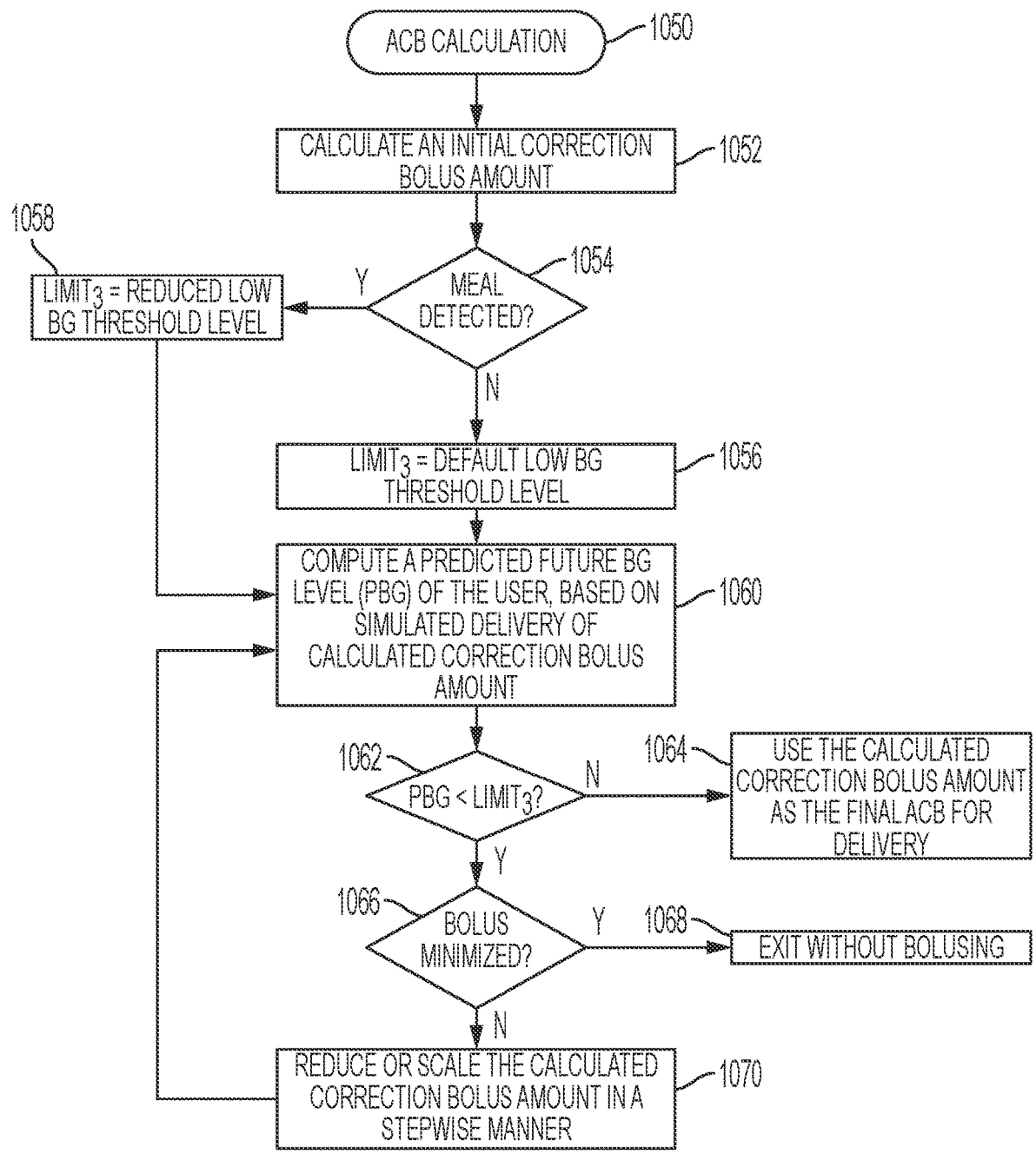
FIG. 11 is a flow diagram that illustrates an exemplary embodiment of a process for calculating an automatic correction bolus.

FIG. 11 is a flow diagram that illustrates an exemplary embodiment of an ACB calculation process 1050, which can be performed during task 1010 of the process 1000 (see FIG. 10). The process 1050 is one suitable methodology for calculating the final ACB amount to be considered for delivery to the user. Alternative embodiments, however, may utilize different methodologies or approaches to determine a recommended ACB amount.

The exemplary embodiment of the process 1050 calculates an initial correction bolus amount for the user (task 1052). In this regard, the initial correction bolus can be calculated in accordance with Equation 1. The exemplary embodiment described here includes an optional feature that automatically detects a BG trend that is indicative of meal consumption and, in response to such detection, adjusts the methodology by which the final ACB amount is calculated. In this regard, FIG. 11 includes a query task 1054 that checks whether the user's BG measurements are indicative of meal consumption. In practice, the process 1050 analyzes the current BG measurement and at least one historical BG measurement to check whether those measurements reflect a BG trend that is indicative of meal consumption by the user. As explained above, if the BG measurements under analysis exhibit a sharp rise over time, a slope that exceeds a threshold value, or the like, then the process 1050 will indicate that a meal has been detected for purposes of query task 1054 (the "Yes" branch); if not, then the process 1050 continues via the "No" branch of query task 1054.

If query task 1054 detects conditions indicative of meal consumption, then the process 1050 continues by reducing a default value of a low BG threshold level to obtain a reduced value (task 1058). The resulting low BG threshold value, which is labeled $LIMIT_3$ in FIG. 11, is utilized as a comparison value in the manner described in more detail below with reference to query task 1062. If query task 1054 determines that the user's BG trend does not reflect the recent consumption of a meal (the "No" branch of query task 1056), then the process 1050 continues with the default, unadjusted, value of the low BG threshold level (task 1056). Accordingly, the default low BG threshold level is utilized to calculate the final ACB amount unless the process 1050 detects conditions that indicate meal consumption—if so, the default low BG threshold level is lowered. As mentioned above, for the exemplary embodiment described here, the default low BG threshold value is 80 mg/dL and the reduced low BG threshold value is 50 mg/dL. It should be appreciated that these thresholds may vary from one embodiment to another, and that the thresholds may be fixed values, automatically adjustable values, or manually adjustable values if so desired.

After settling on the value to be used for the low BG threshold level ($LIMIT_3$), the process 1050 continues by computing a predicted future BG level (PBG) of the user, which results from simulated delivery of the calculated correction bolus amount (task 1060). In accordance with the exemplary embodiment presented here, the process 1050 calculates a set of predicted or forecasted glucose measurement values for the patient corresponding to a time period into the future and simulates delivery of the initial correction bolus amount (obtained at task 1052). The resulting PBG can be calculated as a function of the current BG measurement value, the current BG measurement derivative or trend, historical insulin delivery, the amount of carbohydrates associated with a detected or announced meal, and the amount of insulin for the correction bolus to be administered. Additionally, the PBG may account for estimated future insulin deliveries that may be automatically or autonomously delivered by the control scheme implemented by the insulin infusion device.

In exemplary embodiments, future glucose values are predicted using a mathematical model of the patient that characterizes the glucose response to insulin delivery by a set of differential equations. Meal information could also be incorporated into the predictions, but the described methodology is more conservative if the influence of carbohydrates on blood glucose is ignored. These equations may be based on a mass balance between estimated glucose utilization as result of insulin delivery. The mathematical model may also include specific parameters that enable it to predict the blood glucose at fasting.

The process 1050 uses the PBG for purposes of scaling the initial correction bolus amount (if needed) to obtain a final correction bolus amount for the user. The goal of the scaling is to reduce the initial correction bolus amount such that the PBG resulting from simulated delivery of the final correction bolus amount exceeds the low BG threshold level. The embodiment described here reduces the initial correction bolus amount in a stepwise (iterative) manner to obtain the final correction bolus amount. Thus, the final correction bolus amount can be equal to or less than the initial correction bolus amount.

FIG. 11 depicts an exemplary embodiment that iteratively reduces the initial correction bolus amount in a stepwise manner such that the scaling maximizes the final correction bolus amount without causing the PBG to fall below the low BG threshold level. In this regard, a query task 1062 of the process 1050 compares the PBG against the low BG threshold level (which may be its default value or the reduced value, as explained above). If the PBG is not lower than the low BG threshold level (the "No" branch of query task 1062), then the calculated correction bolus amount is used as the final ACB for delivery (task 1064). For the first iteration of the methodology, the calculated correction bolus amount is equal to the initial correction bolus amount calculated at task 1052. For subsequent iterations of the methodology, the calculated correction bolus amount will be less than the initial amount.

If the PBG is lower than the low BG threshold value (the "Yes" branch of query task 1062), then the process 1050 checks whether the calculated correction bolus amount has reached a minimum value (query task 1066). The minimum value may be any defined amount of insulin, a percentage of the initially calculated correction bolus amount, or the like. For example, the minimum bolus value considered at query task 1066 may be zero Units of insulin. If the calculated correction bolus amount for the current iteration of the methodology has reached the minimum value (the "Yes" branch of query task 1066), then the process 1050 exits without delivering a correction bolus to the user (task 1068), or sets the final ACB amount to be equal to the minimum value, e.g., zero Units.

If the calculated correction bolus amount for the current iteration of the methodology has not reached the minimum value (the "No" branch of query task 1066), then the correction bolus amount is reduced or scaled down, preferably in a stepwise manner (task 1070). The type and amount of scaling/reduction may vary from one implementation to another, and different techniques can be used. The embodiment described here employs a simple scaling factor (multiplier) to progressively reduce the initial correction bolus amount as needed. More specifically, the first comparison at query task 1062 considers the unscaled initial correction bolus amount (i.e., 100% of the initial correction bolus amount), the second iteration of query task 1062 considers 75% of the initial correction bolus amount, the third iteration of query task 1062 considers 50% of the initial correction bolus amount, the fourth iteration of query task 1062 considers 25% of the initial correction bolus amount, and the fifth iteration of query task 1062 considers 0% of the initial correction bolus amount (i.e., no correction bolus). Ultimately, the scaling step multiplies the initial correction bolus amount by a scaling factor between 0.0 and 1.0, inclusive, to obtain the final correction bolus amount.

In other embodiments, a golden ratio-based search or a Fibonacci search is utilized to progressively or iteratively reduce the search space defined by the initial correction bolus amount using intermediate values within the search space that progressively converge toward an adjusted bolus amount that is selected to be administered in lieu of the initial correction bolus amount. In this regard, in exemplary embodiments, the search attempts to maximize the final correction bolus dosage within the search space defined by the initial correction bolus amount while maintaining a predicted future glucose level for the patient that satisfies a postprandial hypoglycemic threshold during a predefined postprandial analysis time period. The bolus search process identifies or otherwise determines an initial adjusted bolus amount to be used to probe or test for use in lieu of the initial correction bolus amount that was originally determined (e.g., at task 1052). In this regard, the bolus search process identifies the initial adjusted bolus amount within a search space defined by a bolus of zero as a lower limit and an upper limit equal to the initial correction bolus amount ($b_{corr}$).

In exemplary embodiments, the golden ratio is utilized to identify the initial adjusted bolus amount as a fraction of the initial correction bolus amount corresponding to the golden ratio by multiplying the initial correction bolus amount by 0.618. That said, the subject matter described herein is not intended to be limited to any particular manner for dividing the search space. The bolus search process also utilizes the initial adjusted bolus amount to define or otherwise determine search spaces for subsequent analysis. For example, an upper search space may be defined relative to the initial adjusted bolus amount as being bounded by the initial adjusted bolus amount as its lower limit and the initial correction bolus amount as its upper limit (e.g., [$0.618b_{corr}$, $b_{corr}$]), while a lower search space may be bounded by the initial adjusted bolus amount as its upper limit and a bolus dosage of zero as its lower limit (e.g., [$0, 0.618b_{corr}$]). This methodology can be used during each iteration of the described methodology to progressively adjust the correction bolus amount and arrive at the final ACB amount.

After reducing the calculated correction bolus amount (at task 1070), the process 1050 returns to task 1060 to compute another PBG, based on simulated delivery of the reduced correction bolus amount. Thereafter, the process 1050 continues in the manner described above. The stepwise scaling of the initial correction bolus amount results in a "maximized" correction bolus that should not result in a BG level that goes below the applicable low BG threshold level for the user. Assuming that a nonzero final correction bolus amount is eventually obtained at task 1064, the ACB calculation process 1050 exits and leads to task 1012 of the insulin infusion device control process 1000 (see FIG. 10 and the relevant description of tasks 1010 and 1012).

For the sake of brevity, conventional techniques related to glucose sensing and/or monitoring, bolusing, closed-loop glucose control, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A system comprising:
   one or more processors; and
   one or more processor-readable storage media storing instructions which, when executed by the one or more processors, cause performance of:
      determining that a current glucose level exceeds a threshold value for delivery of a correction bolus;
      calculating an amount of insulin for the correction bolus;
      predicting a future glucose level that would result from delivery of the calculated amount of insulin for the correction bolus;
      comparing the future glucose level to a threshold level for hypoglycemia; and
      causing delivery of the correction bolus in the calculated amount when the future glucose level exceeds the threshold level for hypoglycemia.

2. The system of claim 1, wherein predicting the future glucose level comprises simulating delivery of the calculated amount of insulin for the correction bolus.

3. The system of claim 1, wherein predicting the future glucose level comprises modeling a patient's glycemic response to insulin delivery.

4. The system of claim 1, wherein calculating the amount of insulin comprises determining a difference between the current glucose level and a target glucose level.

5. The system of claim 1, wherein calculating the amount of insulin comprises determining a current amount of active insulin.

6. The system of claim 1, wherein calculating the amount of insulin comprises determining an insulin sensitivity factor.

7. The system of claim 1, wherein calculating the amount of insulin comprises:
   calculating a potential amount of insulin for the correction bolus;
   determining a predicted glucose level that would result from delivery of the potential amount of insulin for the correction bolus;
   comparing the predicted glucose level to the threshold level for hypoglycemia; and
   scaling down the potential amount of insulin when the predicted glucose level does not exceed the threshold level for hypoglycemia.

8. The system of claim 1, wherein the one or more processor-readable storage media further store instructions which, when executed by the one or more processors, cause performance of:
   prior to calculating the amount of insulin for the correction bolus, determining that a maximum basal delivery rate has been reached.

9. The system of claim 1, wherein the current glucose level is obtained from a continuous glucose monitoring device.

10. The system of claim 1, wherein the one or more processor-readable storage media further store instructions which, when executed by the one or more processors, cause performance of:
    prior to causing delivery of the correction bolus in the calculated amount, determining that the calculated amount exceeds a minimum bolus delivery amount.

11. The system of claim 1, wherein the one or more processor-readable storage media further store instructions which, when executed by the one or more processors, cause performance of:
    prior to predicting the future glucose level, determining whether the current glucose level is indicative of meal consumption; and
    determining the threshold level for hypoglycemia based on reducing a default threshold level for hypoglycemia when the current glucose level is indicative of meal consumption.

12. A processor-implemented method comprising:
    determining that a current glucose level exceeds a threshold value for delivery of a correction bolus;
    calculating an amount of insulin for the correction bolus;
    predicting a future glucose level that would result from delivery of the calculated amount of insulin for the correction bolus;
    comparing the future glucose level to a threshold level for hypoglycemia; and
    causing delivery of the correction bolus in the calculated amount when the future glucose level exceeds the threshold level for hypoglycemia.

13. The method of claim 12, wherein predicting the future glucose level comprises simulating delivery of the calculated amount of insulin for the correction bolus.

14. The method of claim 12, wherein predicting the future glucose level comprises modeling a patient's glycemic response to insulin delivery.

15. The method of claim 12, wherein calculating the amount of insulin comprises one or more of:
    determining a difference between the current glucose level and a target glucose level;
    determining a current amount of active insulin; and
    determining an insulin sensitivity factor.

16. The method of claim 12, wherein calculating the amount of insulin comprises:
    calculating a potential amount of insulin for the correction bolus;
    determining a predicted glucose level that would result from delivery of the potential amount of insulin for the correction bolus;
    comparing the predicted glucose level to the threshold level for hypoglycemia; and
    scaling down the potential amount of insulin when the predicted glucose level does not exceed the threshold level for hypoglycemia.

17. The method of claim 12, further comprising:
    prior to calculating the amount of insulin for the correction bolus, determining that a maximum basal delivery rate has been reached.

18. The method of claim 12, further comprising:
    prior to causing delivery of the correction bolus in the calculated amount, determining that the calculated amount exceeds a minimum bolus delivery amount.

19. The method of claim 12, further comprising:
    prior to predicting the future glucose level, determining whether the current glucose level is indicative of meal consumption; and determining the threshold level for hypoglycemia based on reducing a default threshold level for hypoglycemia when the current glucose level is indicative of meal consumption.

20. One or more non-transitory processor-readable storage media storing instructions which, when executed by one or more processors, cause performance of:

determining that a current glucose level exceeds a threshold value for delivery of a correction bolus;

calculating an amount of insulin for the correction bolus;

predicting a future glucose level that would result from delivery of the calculated amount of insulin for the correction bolus;

comparing the future glucose level to a threshold level for hypoglycemia; and causing delivery of the correction bolus in the calculated amount when the future glucose level exceeds the threshold level for hypoglycemia.

\* \* \* \* \*